(12) United States Patent
Lin

(10) Patent No.: US 7,410,650 B2
(45) Date of Patent: Aug. 12, 2008

(54) METHOD OF FABRICATING NANO-SILVER FIBERS

(75) Inventor: Jia-Peng Lin, Hsin Chuang (TW)

(73) Assignee: Taiwan Textile Research Institute, Tu-Chen, Taipei Hsien (TW)

( * ) Notice: Subject to any disclaimer, the term of this patent is extended or adjusted under 35 U.S.C. 154(b) by 175 days.

(21) Appl. No.: 11/335,356

(22) Filed: Jan. 19, 2006

(65) Prior Publication Data

US 2006/0202382 A1 Sep. 14, 2006

(30) Foreign Application Priority Data

Mar. 9, 2005 (TW) ............................ 94107209 A

(51) Int. Cl.
- *A01N 25/00* (2006.01)
- *A01N 25/34* (2006.01)
- *A01N 25/12* (2006.01)
- *A01N 59/16* (2006.01)
- *D01F 1/10* (2006.01)
- *D01F 6/00* (2006.01)
- *D02G 3/00* (2006.01)
- *D06M 23/10* (2006.01)
- *C08K 3/02* (2006.01)

(52) U.S. Cl. ................ 424/402; 424/489; 424/618; 424/619; 427/304; 427/443.1; 106/1.19; 428/361; 428/364; 428/365

(58) Field of Classification Search .............. 424/402, 424/489

See application file for complete search history.

(56) References Cited

U.S. PATENT DOCUMENTS

| 6,524,505 | B1 | 2/2003 | Bisognin et al. | |
|---|---|---|---|---|
| 6,685,957 | B1 | 2/2004 | Bezemer et al. | |
| 6,979,491 | B2 * | 12/2005 | Yan et al. | 428/361 |
| 2003/0185889 | A1 * | 10/2003 | Yan et al. | 424/484 |
| 2007/0003603 | A1 * | 1/2007 | Karandikar et al. | 424/443 |

FOREIGN PATENT DOCUMENTS

JP 09-059820 3/1997

OTHER PUBLICATIONS

HCAPLUS abstract 1997:293965; abstracting JP 9-059820 (1997).*
Etris, S., "Silver and Silver Alloys," in: Kirk-Othmer Encyclopedia of Chemical Technology (online), John Wiley & Sons, NY pp. 1, 9 and 10. Published online Sep. 14, 2001. URL:<http://www.mrw.interscience.wiley.com/emrw/9780471238966/home>.*
Nersisyan, H.H. et al., "A new and effective chemical reduction method for preparation of nanosized silver powder and colloid dispersion," Materials Research Bulletin, vol. 38, pp. 949-956 (2003).*

* cited by examiner

*Primary Examiner*—John Pak
(74) *Attorney, Agent, or Firm*—Patterson & Sheridan, L.L.P.

(57) ABSTRACT

A method of fabricating nano-silver fibers is provided. An organic solution of a dispersant is prepared. Then, a silver salt and a reductant are added into the organic solution. The organic solution is stirred to let the silver salt and the reductant react to form silver nanoparticles dispersed in the organic solution uniformly. Next, a spinnable polymer resin is dissolved in the organic solution to form a spinning solution. A wet spinning method is performed to let the spinning solution form nano-silver fibers.

13 Claims, No Drawings

METHOD OF FABRICATING NANO-SILVER FIBERS

CROSS-REFERENCE TO RELATED APPLICATIONS

The present application is based on, and claims priority from, Taiwan Application Serial Number 94107209, filed Mar. 9, 2005, the disclosure of which is hereby incorporated by reference herein in its entirety.

BACKGROUND OF THE INVENTION

1. Field of Invention

The present invention relates to a method of fabricating antibacterial fibers. More particularly, the present invention relates to a wet spinning method of fabricating nano-silver fibers.

2. Description of Related Art

As living standards have increased, antibacterial requirements for sanitary articles, daily-use articles, water treatment apparatuses, and food packaging have also increased. Therefore, adding antibacterial agents in these articles and apparatuses have become increasingly more welcomed by consumers. Among the applications, the earliest application of antibacterial textiles was during the Second World War. The percentage of injured persons becoming infected was thus largely decreased.

The commonly used spinning method can be divided into three classes: melt spinning, dry spinning and wet spinning. Wet spinning can be easily performed at a relatively low temperature and hence is quite economic. Therefore, wet spinning is widely used to fabricate acrylic fibers and Rayon fibers. If wet spinning could be used to fabricate antibacterial fibers, a large profitability could be obtained.

There are some methods of fabricating antibacterial fibers by wet spinning developed in the prior arts. For example, in U.S. Pat. No. 6,524,505, chitosan is used as an antibacterial agent. The chitosan is dissolved in water first. After processing acrylonitrile polymer to form acrylic fibers, the acrylic fibers are immersed in the aqueous solution of chitosan to allow chitosan to coat on the acrylic fibers.

In U.S. Pat. No. 6,685,957, an antibacterial agent with bioactivity is dissolved in water. The aqueous solution of the antibacterial agent is added to an organic phase of a spinning solution to form an emulsion. The emulsion is flowed out from outlets of a spinning apparatus into a water tank to form antibacterial fibers.

In Japan Publication No. 09-059820, titanium dioxide is used as an antibacterial agent. Titanium dioxide powder is dispersed in an organic solvent to form a suspension solution. The suspension solution is mixed with an organic solution of acrylonitrile copolymer. Then, wet spinning is performed to get antibacterial fibers.

As with the descriptions above, wet spinning is performed after mixing an antibacterial agent and a spinning solution in most prior arts. However, either the particle size of the antibacterial agent is too large or it is difficult for the antibacterial agent to disperse in the spinning solution. Therefore, the antibacterial agent cannot be dispersed in the spinning solution uniformly. This usually requires the amount of the antibacterial agent added to the spinning solution to be multiple weight percents to enable the obtained fibers to have antibacterial ability. Moreover, the obtained antibacterial fibers are not water-wash resistant. Consequently, the antibacterial ability of the obtained antibacterial fibers is largely decreased after washing with water.

SUMMARY OF THE INVENTION

In one aspect, the present invention provides a method of fabricating nano-silver fibers to allow silver nanoparticles tightly adhering on the fibers.

In accordance with the foregoing and other aspects of the present invention, a method of fabricating nano-silver fibers is provided. First, a dispersant solution is prepared by dissolving a dispersant in an organic solvent. Next, a silver salt and a reductant are added into the dispersant solution. The dispersant solution is then stirred to form silver nanoparticles by reacting the silver salt with the reductant and to distribute the silver nanoparticles in the organic solution uniformly. A polymer resin for spinning is added into the organic solution to form a spinning solution. A wet spinning process is used to spin the spinning solution to obtain nano-silver fibers.

According to a preferred embodiment, the dispersant described above is, for example, a surfactant, such as sodium dodecyl sulfate or cetyltrimethylammonium bromide, or a water-soluble polymer, such as polyvinyl pyrrolidone or polyvinyl alcohol. The organic solvent is, for example, N,N-dimethylformamide, N,N-dimethylacetamide, or dimethyl sulfoxide.

The silver salt described above is $CH_3COOAg$, $AgNO_2$, $AgNO_3$, $AgCl$, or $Ag_2SO_4$. The reductant is sodium borohydride, hydrazine hydrate, or sodium citrate. The reaction of the silver salt and the reductant is preferably performed at a temperature of about 20-80° C. for about 0.5-3 hours. The concentration and diameter of silver nanoparticles in the prepared organic solution is about 100-10,000 ppm and less than 100 nm, respectively.

The polymer resin described above is, for example, acrylic resin or acrylonitrile resin. The concentration of silver nanoparticles in the obtained nano-silver fibers is about 20-500 ppm.

In the foregoing, preparing silver nanoparticles in the organic solution of a dispersant can distribute the silver nanoparticles in the organic solution uniformly. Then, a spinnable polymer resin is added into the organic solution to form a spinning solution. Next, a wet spinning process is performed to spin the spinning solution to form nano-silver fibers. Since silver nanoparticles and the polymer resin can be uniformly mixed in the organic solution, the silver nanoparticles and the fibers in the nano-silver fibers have strong adhesion with each other. Therefore, the silver nanoparticles cannot easily separate from the fibers even after longtime usage or washing with water many times. That is, the nano-silver fibers can be used to fabricate an antibacterial textile of low price and long efficacy.

It is to be understood that both the foregoing general description and the following detailed description are made by use of examples and are intended to provide further explanation of the invention as claimed.

DETAILED DESCRIPTION OF THE PREFERRED EMBODIMENTS

This invention provides a method of fabricating nano-silver fibers by combining technologies of fabricating nanoparticles and wet spinning.

First, an organic solution of a dispersant is prepared to let the dispersant dissolve in the organic solution. A silver salt and a reductant are then added into the organic solution of the dispersant. The organic solution is stirred to allow the silver salt reacting with the reductant to form silver nanoparticles dispersed in the organic solution uniformly. Next, a spinnable polymer resin is added and dissolved in the organic solution of the silver nanoparticles to form a spinning solution. A conventional wet spinning process is used to spin the spinning solution to form nano-silver fibers.

According to a preferred embodiment of the present invention, the dispersant is, for example, a surfactant or a water-soluble polymer. The surfactant is sodium dodecyl sulfate (SDS) or cetyltrimethylammonium bromide (CTAB). The water-soluble polymer is polyvinyl pyrrolidone (PVP) or polyvinyl alcohol (PVA). The organic solvent described above is, for example, N,N-dimethylformamide (DMF), N,N-dimethylacetamide (DMAc), or dimethyl sulfoxide (DMSO). The function of the dispersant is preventing the prepared silver nanoparticles from aggregating in the organic solution; hence, the silver nanoparticles can be dispersed in the organic solution uniformly.

The silver salt described above is $CH_3COOAg$, $AgNO_2$, $AgNO_3$, $AgCl$, or $Ag_2SO_4$. The reductant is sodium borohydride ($NaBH_4$), hydrazine hydrate ($N_2H_4 \cdot H_2O$), or sodium citrate. The reaction of the silver salt and the reductant is preferably performed at a temperature of about 20-80° C. for about 0.5-3 hours. The concentration and diameter of silver nanoparticles in the prepared organic solution is about 100-10,000 ppm and less than 100 nm, respectively.

The polymer resin described above is, for example, acrylic resin or acrylonitrile resin. The polymer is dissolved in the organic solution at a temperature of about 50-80° C. for about 0.5-3 hours. The concentration of silver nanoparticles in the obtained nano-silver fibers is about 20-500 ppm.

Embodiment 1

3 g of PVP, 1.27 g of silver nitrate, and 0.03 g of sodium borohydride were sequentially dissolved in 100 mL of DMAc to form an organic solution. The organic solution was then stirred at room temperature for about 30 minutes to get an organic solution of silver nanoparticles. The concentration of the silver nanoparticles in the organic solution was about 8000 ppm.

The concentration of the silver nanoparticles in the organic solution was diluted to about 80 ppm by adding more DMAc. Then, acrylonitrile resin of fiber grade was added into the organic solution of the silver nanoparticles. The acrylonitrile was dissolved at a temperature of about 80° C. to form a spinning solution containing about 15 wt % of silver nanoparticles—acrylonitrile resin. The spinning solution was flowed out from spinneret into a water tank to perform phase transition. After stretching and drying, nano-silver fibers with excellent antibacterial function were obtained.

Embodiment 2

3.3 g of SDS, 0.67 g silver chloride, and 0.04 g of hydrazine hydrate were sequentially dissolved in 100 mL of DMF to form an organic solution. The organic solution was then stirred at room temperature for about 30 minutes to get an organic solution of a silver nanoparticles. The concentration of the silver nanoparticles in the organic solution was about 5000 ppm.

The concentration of the silver nanoparticles in the organic solution was diluted to about 80 ppm by adding more DMF. Then, acrylonitrile resin was added into the organic solution of the silver nanoparticles. The acrylonitrile in the fiber grade was dissolved at a temperature of about 80° C. to form a spinning solution containing about 15 wt % of silver nanoparticles—acrylonitrile resin. The spinning solution was flowed out from spinneret into a water tank to perform phase transition. After stretching and drying, nano-silver fibers with excellent antibacterial function were obtained.

Antibacterial Test

The nano-silver fibers obtained above were woven to form an antibacterial textile containing about 100 ppm of silver nanoparticles. The antibacterial textile made by nano-silver fibers was then subjected to an antibacterial test, and the results are listed in the following tables.

| Tested Item | | Before washing | After washing 50 times |
|---|---|---|---|
| Staphylococcus Aureaus (ATCC 6538P) | Bacteriostatic value | >5.26 | 4.15 |
| | Bactericidal value | >3.01 | 1.54 |
| Klebsiella Pneumoniae (ATCC 4352) | Bacteriostatic value | >6.03 | 4.50 |
| | Bactericidal value | >2.99 | 1.28 |

According to the bacteriostatic standard of the Japanese Association for the Functional Evaluation of Textiles (JAFET), a textile is bacteriostatic when the bacteriostatic value is larger than 2.2, and a textile is bactericidal when the bactericidal value is larger than zero. Hence, from the table above, the bacteriostatic and bactericidal values of the textiles made by nano-silver fibers are much larger than the standard values. It is proof that the antibacterial textile made by nano-silver fibers has outstanding bacteriostatic and bactericidal ability. Even after washing 50 times, the bacteriostatic and bactericidal values of the textile made by nano-silver fibers are still larger than the standard values. That is, the enduring washability of the textile made by nano-silver fibers is also very good.

In the foregoing, preparing silver nanoparticles in the organic solution of a dispersant can distribute the silver nanoparticles in the organic solution uniformly. Then, a spinnable polymer resin is added into the organic solution to form a spinning solution. Next, a wet spinning is performed to spin the spinning solution to form nano-silver fibers. Since silver nanoparticles and the polymer resin can be uniformly mixed in the organic solution, the silver nanoparticles and the fibers in the nano-silver fibers have strong adhesion with each other. Therefore, the silver nanoparticles cannot easily separate from the fibers even after longtime usage or washing with water many times. That is, the nano-silver fibers can be used to fabricate an antibacterial textile of low price and long efficacy.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of fabricating nano-silver fibers, comprising:
    dissolving a dispersant in an organic solvent to form a dispersant solution;
    adding a silver salt to the dispersant solution;
    adding a reductant to the dispersant solution;
    stirring the disperant solution containing the silver salt and the reductant to form a nano-silver solution, wherein a concentration of silver nanoparticles in the nano-silver solution is about 100-10,000 ppm;

dissolving a spinnable polymer resin for spinning in the nano-silver solution to form a spinning solution; and spinning the spinning solution to form nano-silver fibers by wet spinning.

2. The method of claim 1, wherein the dispersant is a surfactant or a water-soluble polymer.

3. The method of claim 2, wherein the surfactant is sodium dodecyl sulfate or cetyltrimethylammonium bromide.

4. The method of claim 2, wherein the water-soluble polymer is polyvinyl pyrrolidone or polyvinyl alcohol.

5. The method of claim 1, wherein the organic solvent is N,N-dimethylformamide, N,N-dimethylacetamide, or dimethyl sulfoxide.

6. The method of claim 1, wherein the silver salt is $CH_3COOAg$, $AgNO_2$, $AgNO_3$, $AgCl$, or $Ag_2SO_4$.

7. The method of claim 1, wherein the reductant is sodium borohydride, hydrazine hydrate, or sodium citrate.

8. The method of claim 1, wherein a temperature of forming the nano-silver solution is about 20-80° C.

9. The method of claim 1, wherein a reaction period of forming the nano-silver solution is about 0.5-3 hours.

10. The method of claim 1, wherein a diameter of silver nanoparticles in the nano-silver solution is less than 100 nm.

11. The method of claim 1, wherein the polymer resin is acrylic resin or acrylonitrile resin.

12. The method of claim 1, wherein a temperature of dissolving the polymer resin is about 50-80° C.

13. The method of claim 1, wherein a concentration of silver nanoparticles in the nano-silver fibers is about 20-500 ppm.

* * * * *